United States Patent [19]

Seifert et al.

[11] 4,182,918

[45] Jan. 8, 1980

[54] PROCESS FOR THE PREPARATION OF POLYHYDRIC PHENOLS

[75] Inventors: Hermann Seifert, Cologne; Helmut Waldmann; Wulf Schwerdtel, both of Leverkusen; Wolfgang Swodenk, Odenthal, all of Fed. Rep. of Germany

[73] Assignee: Bayer Aktiengesellschaft, Leverkusen, Fed. Rep. of Germany

[21] Appl. No.: 857,623

[22] Filed: Dec. 5, 1977

[30] Foreign Application Priority Data

Dec. 24, 1976 [DE] Fed. Rep. of Germany ....... 2658866

[51] Int. Cl.$^2$ ........................................... C07C 39/08
[52] U.S. Cl. ................................... 568/771; 568/707; 568/622; 568/741; 568/775
[58] Field of Search ........................... 260/621 G, 625; 568/771, 707, 775, 622, 741

[56] References Cited

U.S. PATENT DOCUMENTS 3,950,437  4/1976  Imamura et al. ................ 260/621 G
4,066,707  1/1978  Nakatani et al. ................ 260/621 G

FOREIGN PATENT DOCUMENTS 1479354  3/1966  France ................................ 260/621 G

*Primary Examiner*—Werren B. Lone
*Attorney, Agent, or Firm*—Sprung, Felfe, Horn, Lynch & Kramer

[57] ABSTRACT

A process has been invented for the preparation of dihydric substituted phenols which comprises reacting a solution, which is essentially anhydrous and free from hydrogen peroxide, of a percarboxylic acid in an inert organic solvent with a monohydric substituted phenol, which is derived from benzene, naphthalene or anthracene and still contains at least one free hydrogen atom in the aromatic nucleus, at temperatures from about $-20°$ C. to about 120° C.

The dihydric substituted phenols obtained according to the invention are known, important industrial intermediate products used in the fields of photography, dyestuffs and plastics, as well as in the scent and flavoring areas.

19 Claims, No Drawings

PROCESS FOR THE PREPARATION OF POLYHYDRIC PHENOLS

The present invention relates to a process for the industrial preparation of dihydric substituted phenols.

Polyhydric phenols are aromatic compounds, the aromatic nucleus of which contains several hydroxyl groups. The most important polyhydric phenols are those which have two hydroxyl groups and are derived from benzene, naphthalene, anthracene or phenanthrene. These dihydric phenols are important industrial intermediate products which are used in large amounts in the field of photography and of dyestuffs and plastics and in the field of scents and flavourings.

In accordance with the great industrial importance of these compounds, there have in the past been no lack of numerous attempts to discover simple processes for their preparation which allow these compounds to be prepared on an industrial scale, avoiding intermediate stages and by-products which pollute the environment.

Thus, for example, the most simple representatives of polyhydric phenols, that is to say the dihydric phenols pyrocatechol and hydroquinone, which are derived from benzene, are today prepared industrially by processes which proceed by the most varied intermediate stages (K. Weissermel and H. J. Arpe, "Industrielle Organische Chemie" ("Industrial Organic Chemistry"), (Verlag Chemie) Weinheim 1976, page 298–302).

In order to obtain hydroquinone, for example, benzene must first be nitrated, after which the corresponding intermediate stage, that is to say nitrobenzene, is then reduced to aniline. The aniline is then in turn reacted with manganese dioxide in aqueous sulphuric acid to give p-benzoquinone ("Ullmanns Enzyklopädie der technischen Chemie" ("Ullmann's Encyclopedia of Industrial Chemistry"), Volume 8, (Urban and Schwarzenberg) Munich 1957, page 741) and this is reduced to hydroquinone using iron.

In order to prepare pyrocatechol, phenol is reacted with chlorine to give 2-chlorophenol, and this is subjected to alkali fusion, an alkali metal chloride being obtained as a by-product which pollutes the environment (Louis F. Fiesel and M. Fieser, "Organische Chemie" ("Organic Chemistry"), (Verlag Chemie) Weinheim 1965, page 915).

A further process for the preparation of pyrocatechol uses phenol-o-sulphonic acid as the intermediate stage, which must also be subjected to alkali fusion (Carl R. Noller, "Lehruch der organischen Chemie" ("Textbook of Organic Chemistry"), (Springer-Verlag) Berlin 1960, page 545).

More recent processes attempt to introduce the second hydroxyl group into the phenol directly by means of hydrogen peroxide, avoiding intermediate stages. However, catalysts are required for this reaction between hydrogen peroxide and phenol in order to activate the hydrogen peroxide In processes in which metal salts, preferably salts of transition metals, are used as the catalyst, there is always the danger that oxidation of the aromatic ring, which proceeds further and leads as far as quinones or degradation products of phenol, occurs as a side reaction, which considerably lowers the industrial value of these processes.

Satisfactory yields of polyhydric phenols are only obtained in a procedure which excludes an industrial application.

Thus, A. Chwala and co-workers (J. Prakt. Chem. 152, 46 (1939) could obtain the dihydric phenols pyrocatechol and hydroquinone in 72% yield in the reaction of phenol with hydrogen peroxide in a very dilute, aqueous solution containing sulphuric acid, using iron sulphate as the catalyst. However, very long reaction times and a reaction temperature of 0° C. are necessary for this. In addition, carrying out the process in a very dilute, aqueous medium entails considerable difficulties in isolating the dihydric phenols from the reaction mixture.

In a further process, the industrial utilisation of which would present considerable difficulties, the use of strong acids as catalysts for the reaction of phenol with hydrogen peroxide is proposed, according to German Auslegeschrift (German Published Specification) 2,064,497. In this procedure, however, in order to achieve yields of about 70%, relative to the hydrogen peroxide employed, it is necessary to employ aqueous $H_2O_2$ in concentrations far above 90% strength. The use of such high concentrations of $H_2O_2$ is associated with the danger of explosion and necessitates extensive and expensive safety measures in the case of an industrial process. A further disadvantage of this process is that the problem of the separation of the acid used as the catalyst from the reaction mixture is not always satisfactorily solved in the sense of an industrial application. In the process according to German Auslegeschrift (German Published Specification) 2,064,497, an equimolar amount of water is also formed from the hydrogen peroxide during the reaction, and this makes the separation of the phenol employed in excess difficult, because of the water/phenol azeotrope, and leads to effluents containing phenol, which can be purified only with considerable technical effort.

According to German Pat. No. 1,543,830, it should be possible to avoid the difficulties which occur when working with highly concentrated aqueous hydrogen peroxide if, for introducing a hydroxyl group into the ring of aromatic compounds, hydrogen peroxide is used as a very dilute organic solution in the presence of boric acid or boric acid derivatives and the resulting boric acid esters of the hydroxylated aromatic compounds are then saponified. However, using boric acid derivatives as hydrogen peroxide activators results in the corresponding boric acid esters first being formed from the hydroxylated aromatic compounds during the reaction, and these must then be saponified in a subsequent process step. The expense connected with this is the decisive disadvantage of the process. The separation and regeneration of the hydrogen peroxide activator containing boron is also expensive.

Substantial improvements in the hydroxylation of phenolic compounds by means of hydrogen peroxide could be achieved, according to German Offenlegungsschrift (German Published Specification) 2,410,758, by carrying out the reaction of the phenolic compound with non-aqueous hydrogen peroxide, dissolved in an organic solvent or in the phenol, to be hydroxylated, itself, in the presence of catalytic amounts of a strong acid. However, the fundamental disadvantages of a process for the hydroxylation of phenolic compounds with hydrogen peroxide in the presence of a strong acid, as a catalyst, also remain in this process.

These disadvantages are, in particular, complications in separating off the strong acid from the reaction mixture. Attempts to achieve a process for the hydroxylation of phenols without using a strong acid have already been indicated a very long time ago. Thus, G.G. Henderson and co-workers (J. Chem. Soc. (London) 97, 1959 (1910)) have attempted to introduce further hydroxyl groups into phenols by reaction with hydrogen peroxide/acetic acid. In the case of phenol itself, a reaction time of several days at room temperature was necessary in order to obtain a mixture of hydroquinone, pyrocatechol and p-benzoquinone. Very long reaction times were also required to introduce three further hydroxyl groups into the aromatic nucleus of p-tert.-butyl-phenol. In the attempt to convert cresols into polyhydric phenols under these conditions, only small amounts of dihydroxymethylbenzenes were obtained, in addition to a considerable proportion of tarry products. From this publication it can be seen, in particular, that an excess of hydrogen peroxide and temperatures above room temperature had to be strictly avoided.

In German Auslegeschrift (German Published Specification) 1,593,968 it is proposed to carry out the introduction of a further hydroxyl group into phenol using a percarboxylic acid prepared in situ from aqueous hydrogen peroxide and a carboxylic acid in the presence of phosphoric acid, formic acid/$H_2O_2$ mixtures and acetic acid/$H_2O_2$ mixtures preferably being used. Since hydrogen peroxide is employed in the process as an aqueous solution, the reaction mixture to be worked up after the conversion contains amounts of water which are not insignificant. This amount of water introduced into the reaction mixture with the hydrogen peroxide is additionally also increased by the amount of water which is formed during the in situ formation of the percarboxylic acid from the carboxylic acid and hydrogen peroxide according to equation (1).

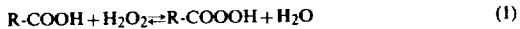

$$R\text{-}COOH + H_2O_2 \rightleftharpoons R\text{-}COOOH + H_2O \qquad (1)$$

Thus, when the $H_2O_2$ is completely converted, equimolar amounts of water, corresponding to the hydrogen peroxide employed in the reaction, are formed and are also contained in the reaction mixture after the reaction has ended. As already mentioned, the presence of water makes the separation of the phenol present in excess in the reaction according to the process of DAS (German Published Specification) 1,593,968 difficult as the result of azeotrope formation, whereby this separation becomes very expensive industrially, in particular when the phenol thus obtained is to be recycled to the reaction, which is appropriate industrially.

However, the difficulties caused by the formation of azeotropic mixtures can already occur in the separation, by distillation, of the carboxylic acid, which has a lower boiling point than phenol, since, as is known, low-molecular carboxylic acids, such as, for example, formic acid and acetic acid, also form azeotropes with water (Robert C. Weast (Editor), "Handbook of Chemistry and Physics", 53rd edition, (The Chemical Rubber Company) Cleveland/Ohio 1972, page D-2, D-25).

In this case also, it is extremely difficult to dehydrate the carboxylic acid industrially in order to be able to re-use it in a suitable form for the reaction with the phenol and the $H_2O_2$.

The working up of the reaction mixture obtained by the process of German Auslegeschrift (German Published Specification) 1,593,968 is also made considerably difficult, from an industrial point of view, that the phosphoric acid additionally necessary to achieve useful yields must be removed again from the reaction mixture by employing an anion exchanger, such as is proposed in this Auslegeschrift (published specification), or by another, additional process step. This means that even in this process the additional presence of a strong acid cannot be dispensed with. Moreover, neither the required reaction times, which are several hours, nor the high temperatures, nor the moderate yields of dihydric phenols make it appear attractive to carry out the process according to DAS (German Published Specification No.) 1,593,968 industrially.

A further disadvantage of the process of DT-AS (German Published Specification No.) 1,593,968 is that the formic acid used for introducing a hydroxyl group into the phenol (the highest yields, connected with the use of phosphoric acid, are only achieved with this acid (compare Examples 1 and 2 of DT-AS (German Published Specification No.) 1,593,968)) occupies a special position amongs the carboxylic acids, with respect to the corrosion problem, which is always of considerable importance in reactions with lower carboxylic acids, because formic acid has a particularly corrosive action, even towards stainless steels.

Summarising, it can be established from the literature on processes for the preparation of polyhydric phenols which has been disclosed hitherto, that all the known processes, including the processes in which hydrogen peroxide or percarboxylic acids are used for introducing further hydroxyl groups into phenolic compounds, for the purpose of preparing polyhydric substituted phenols, are not able to offer a satisfactory solution to the problems set by industrial requirements and the question of profitability.

It has now been found, that particularly dihydric substituted phenols can be prepared in a simple manner which is advantageous industrially and economically, when a solution, which is essentially anhydrous and free from hydrogen peroxide, of a percarboxylic acid in an inert organic solvent is reacted with a monohydric substituted phenol, which is derived from benzene, naphthalene or anthracene and still contains at least one free hydrogen atom in the aromatic nucleus, at temperatures from about $-20°$ C. to about $120°$ C.

In general, one hydroxyl group can be introduced, according to the invention, into the aromatic ring of the monohydric phenolic compounds.

In the hydroxylation of polynuclear phenols, the second hydroxyl group preferably enters into the nucleus already substituted by a hydroxyl group. Thus, there result preferably 1.2-dihydroxynaphthalene from α-naphthol, 1.2-dihydroxynaphthalene from β-naphthol, and 1.2-dihydroxylanthracene from 1-hydroxyanthracene.

The dihydric substituted phenols which follow can be prepared by the process according to the invention: 2-methylhydroquinone, 3-methylpyrocatechol, 4-cyclohexylpyrocatechol, 2-cyclohexylhydroquinone, 3-cyclohexylpyrocatechol, 4-phenylpyrocatechol, 3-phenylpyrocatechol, 2-phenylhydroquinone, 4-ethylpyrocatechol, 3-ethylpyrocatechol, 2-ethylhydroquinone, 3-isopropylpyrocatechol, 2-isopropylhydroquinone, 4-isopropylpyrocatechol, 2-tert.-butylhydroquinone, 3-tert.-butylpyrocatechol, 4-tert.-butylpyrocatechol, 2-nitrohydroquinone, 3-nitropyrocatechol, 4-nitropyrocatechol, 3-bromo-5-methylpyrocatechol, 2-chlorohydroquinone, 3-chloropyrocatechol, 4-chloropyrocatechol, 4-caromethoxypyrocatechol, 3-carboethoxypyrocatechol, 4-dyclopentylpyrocatechol, 3-N,N-dimethylaminopyrocatechol, 2-N,N-dimethylaminohydroquinone, 4-cyanopyrocatechol, 4-methoxypyrocatechol, 3-isopropoxypyrocatechol, 2-ixopropoxyhydroquinone, 4-ethoxypyrocatechol, 3,5-diethylpyrocatechol, 2,6-diethylhydroquinone, 3-isopropyl-6-methylpyrocatechol, 2-isopropyl-5-methylhydroquinone, pyrocatechol, hydroquinone, 3,4-dimethylpyrocatechol, 3,5-dimethylpyrocatechol, 3,6-dimethylpyrocatechol, 4,5-dimethylpyrocatechol, 2,3-dimethylhydroquinone, 2,5-dimethylhydroquinone, 2,6-dimethylhydroquinone, 1,2-dihydronaphthalene, 1,4-dihydroxynaphthalene, 2,3-dihydroxynaphthalene, 1,2-dihydroxy-4-methylnaphthalene, 1,4-dihydroxy-2-methylnaphthalene, 2,3-dihydroxy-1-methylnaphthalene, 1,2-dihydroxy-6-methylnaphthalene, 2,3-dihydroxy-6-methylnaphthalene, 1,2-dihydroxy-4-isopropylnaphthalene, 1,2-dihydroxy-4-t.butylnaphthalene, 1,2-dihydroxy-6-phenylnapthalene, 1,2-dihydroxy-6-methoxynaphthalene, 1,2-dihydroxyanthacene, 1,4-dihydroxyanthracene, 2,3-dihydroxyanthracene, 1,4-dihydroxy-6-methylnaphthalene, 1,4-dihydroxy-6-phenylnaphthalene and 1,4-dihydroxy-6-methoxynaphthalene.

The substituted phenolic compounds into which further hydroxyl group can be introduced by the process according to the invention are monohydric substituted phenols which are derived from benzene, naphthalene or anthracene and still contain at least one free hydrogen atom in the aromatic nucleus. In the case of phenolic compounds which are derived from benzene, this free hydrogen atom is preferably in the 2-position or 4-position relative to the hydroxyl group already present. The aromatic ring on which the substituted phenols are based and into which a further hydroxyl group can be introduced by the process according to the invention can contain, as substituents, one or more identical or different straight-chain or branched aliphatic (e.g. alkyl) radicals containing one to ten carbon atoms, or several cycloaliphatic (e.g. cycloalkyl) radicals containing three to twelve C atoms, or several phenyl or naptyl radicals. In detail, the following hydrocarbon substituents may be mentioned: methyl, ethyl, isopropyl, n-butyl, i-butyl, tert.-butyl, n-pentyl, 2-methylbutyl, 3-methylbutyl, 2-ethylpropyl, n-hexyl, 2-methylpentyl, 3-methylpentyl, 4-methylpentyl, n-heptyl, n-octyl, 2-ethylhexyl, n-nonyl, 2-ethylheptyl, n-decyl, cyclopropyl, cyclobutyl, cyclopentyl, cyclohexyl, cycloheptyl, cyclooctyl, cyclononyl, cyclodecyl, phenyl and naphthyl.

In these substituents, one or more hydrogen atoms of the hydrocarbon radical can in turn be replaced by groups which are stable under the conditions of the reaction of the phenols with the solution of the percarboxylic acid. Examples which may be mentioned of groups of this type are: fluorine, chlorine and bromine atoms and $C_1$ to $C_5$-alkoxy, $C_1$-$C_5$-dialkylamino, carboxyl, nitro, cyano or sulphonic acid groups, or carboalkoxy groups, the alkoxy radicals of which contain one to ten carbon atoms. The aromatic ring of the phenolic compounds which are suitable for the process according to the invention can, however, also be substituted by one or more of the groups listed above.

Preferably, the further hydroxyl group is introduced by the process according to the invention, into the aromatic nucleus of monohydric substituted phenols which are derived from benzene.

For example, phenols of the formula

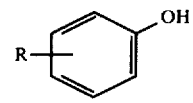

(I)

wherein
R represents $C_1$-$C_{10}$-alkyl, $C_3$-$C_{12}$-cycloalkyl, phenyl, naphthyl, fluorine, chlorine or bromine, or a nitro, cyano, sulphonic acid, carbohydroxyl, carbo-$C_1$-$C_{10}$-alkoxy, $C_1$-$C_3$-alkoxy or $C_1$-$C_4$-dialkylamino group, or R represents said alkyl and cycloalkyl radicals substituted by fluorine, chlorine or bromine atoms or $C_1$-$C_5$-alkoxy, $C_1$ to $C_4$-dialkylamino, carboxyl, nitro, cyano, sulphonic acid or $C_1$ to $C_{10}$-carbalkoxy groups, or R represents said phenyl and naphthyl radicals substituted by fluorine, chlorine, bromine, $C_1$-$C_{10}$-alkyl or $C_3$-$C_{12}$-cycloalkyl, as well as nitro, carbohydroxyl, carbo-$C_1$-$C_{10}$-alkoxy, $C_1$-$C_5$-alkoxy, cyano, sulphonic acid or $C_1$-$C_4$-dialkylamino groups, can be employed in the process according to the invention.

A preferred group of phenolic compounds within the formula (I) correspond to the substituted phenols of the formula

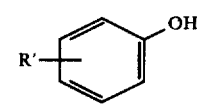

(II)

wherein
R' represents $C_1$-$C_5$-alkyl, $C_5$-$C_7$-cycloalkyl, phenyl, fluorine or chlorine, or a nitro, sulphonic acid, carbohydroxyl, carbo-$C_1$-$C_3$-alkoxy, $C_1$-$C_3$-alkoxy or $C_1$-$C_2$-dialkylamino group.

Substituted monohydric phenols of the formula

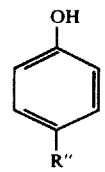

(III)

wherein
R" denotes $C_1$-$C_5$-alkyl, $C_5$-$C_7$-cycloalkyl, phenyl, fluorine or chlorine, or a nitro, sulphonic acid, carbohydroxyl, carbo-$C_1$-$C_3$-alkoxy, $C_1$-$C_3$-alkoxy or $C_1$-$C_2$-dialkylamino group are very particularly preferably used in the process according to the invention.

Examples which may be mentioned of substituted phenols which are suitable for the introduction of a further hydroxyl group into the aromatic ring are: o-cresol, m-cresol, p-cresol, p-cyclohexylphenol, o-cyclohexylphenol, p-phenylphenol, o-phenylphenol, m-phenylphenol, p-ethylphenol, o-ethylphenol, m-ethylphenol, o-isopropylphenol, p-isopropylphenol, o- and p-tert.-butylphenol, p-nitrophenol, o-nitrophenol, m-nitrophenol, 2-bromo-4-methyl-phenol, p-chlorophenol, o-chlorophenol, m-chlorophenol, p-carbomethoxyphenol, salicylic acid ethyl ester, p-cyclopentylphenol, o-dimethylaminophenol, p-cyano-phenol, p-methoxy-phenol, o-isopropoxyphenol, p-ethoxyphenol, 3,5-diethyl-phenol, thymol, phenol, carvacrol, 1,2,3- xylenol, 1,2,4-xylenol, 1,3,2-xylenol, 1,3,4-xylenol, 1,3,5-xylenol, 1,4,2-xylenol, α-naphthol, β-naphthol, 1-hydroxy-4-methylnaphthalene, 1-hydroxy-2-methylnaphthalene, 2-hydroxy-1-methylnaphthalene, 2-hydroxy-6-methylnaphthalene, 1-hydroxy-4-isopropyl-naphthalene, 1-hydroxy-4-t-butylnaphthalene, 1-hydroxy-6-phenyl-naphthalene, 1-hydroxy-6-methoxy-naphthalene, 1-hydroxy-anthracene and 2-hydroxy-anthracene.

In general, the anhydrous solution of the percarboxylic acid used for the process according to the invention, contains not more than about 5% by weight of water. A solution of percarboxylic acid which contains less than about 3% by weight of water is preferred. A solution of percarboxylic acid in the inert organic solvent, the water content of which is below 1% by weight, is particularly preferably used. A solution which contain not more than 0.5% by weight of water is very particularly preferred.

In general, the content of free hydrogen peroxide in the organic solution of the percarboxylic acid which is suitable for the process according to the invention is not more than 2% by weight. A solution which contain less than 1% by weight of hydrogen peroxide is preferably employed. An organic solution which contains less than 0.5% by weight of $H_2O_2$ is very particularly preferably used.

The organic solution of percarboxylic acid which is suitable for the process according to the invention, still contain small amounts of the acid catalyst from the acid-catalysed preparation and in general contain less than 1% by weight of a free strong acid or of salts of these acids, such as, for example, sulphuric acid, methanesulphonic acid, trifluoromethanesulphonic acid, perchloric acid or sulphonic acids of benzene or naphthalene. A solution with a content of strong acid of less than 0.5% by weight is particularly suitable, and an organic solution of percarboxylic acids which contain less than 0.1% by weight of strong acid is very particularly suitable.

The organic solution of percarboxylic acid can also contain free carboxylic acid in addition to the percarboxylic acid. The amount of carboxylic acid which can be present in addition to the percarboxylic acid is not important in the process according to the invention. It can be larger or smaller than the amount of percarboxylic acid in the solution. However, solutions in which the amount of carboxylic acid is less than that of the percarboxylic acid are usually reacted with the phenols. The content of carboxylic acid in the percarboxylic acid solution is, for example, about 1 to 50, preferably about 5 to 40, % by weight.

In some cases it can be advantageous to add a stabiliser to the organic solution of the percarboxylic acid. Stabilisers which can be used are carboxylic acids or polycarboxylic acids containing nitrogen or hydroxyl groups, but also phosphorus compounds, such as, for example, the sodium salts of polyphosphoric acids which are partially esterified by long-chain alcohols (compare D. Swern "Organic Peroxides" Volume 1, page 350, 1st paragraph; Wiley-Interscience 1970). However, in most cases a stabiliser is not necessary since a substantial decomposition of the percarboxylic acid, which impairs the process, does not occur at the temperatures at which the process according to the invention is carried out. There is also an advantage to be seen in this, since in the end the stabiliser is an impurity in the reaction mixture.

The concentration of the percarboxylic acid in the organic solution being reacted with the phenols can vary within wide limits. In general, concentrations of about 3 to 60% by weight are suitable. Solutions which contain about 5 to 50% by weight of percarboxylic acid are preferably used, and those which have a content of carboxylic acid of 10 to 30% by weight are very particularly preferably used.

Percarboxylic acids which are suitable for the process according to the invention are those which are derived from aliphatic (particularly alkanoic), cycloaliphatic (particularly cycloalkanoic) and aromatic (particularly monocyclic and bicyclic carbocyclic aromatic) monocarboxylic or dicarboxylic acids. Examples of possible aliphatic carboxylic acids, the percarboxylic acids of which can be used for the process according to the invention, are: formic acid, acetic acid, propionic acid, butyric acid, isobutyric acid, valeric acid, trimethylacetic acid, caproic acid, heptylic acid, caprylic acid, pelargonic acid, capric acid, undecanoic acid, lauric acid, myristic acid, pentadecanoic acid, palmitic acid, stearic acid, arachic acid, fluoroacetic acid, trifluoroacetic acid, chloroacetic acid, dichloroacetic acid, trichloroacetic acid, α-chloropropionic acid, α-fluoropropionic acid, β-chloropropionic acid, succinic acid, glutaric acid, adipic acid, suberic acid, azelaic acid and sebacic acid. Cycloaliphatic carboxylic acids which may be mentioned which are suitable starting materials for corresponding percarboxylic acids are cyclopentanecarboxylic acid, cyclohexanecarboxylic acid, cycloheptanecarboxylic acid, cyclohexane-1,3-dicarboxylic acid and cyclohexane-1,4-dicarboxylic acid. Examples of possible aromatic carboxylic acids for the corresponding percarboxylic acids are benzoic acid, p-chlorobenzoic acid, phthalic acid, naphthalenecarboxylic acid, benzene-1,3-dicarboxylic acid and benzene-1,4-dicarboxylic acid.

Percarboxylic acids which are derived from aliphatic (particularly alkane) carboxylic acids with 2 to 5 carbon atoms, such as acetic acid, propionic acid, n-butyric acid, isobutyric acid and valeric acid, or trimethylacetic acid and dimethylpropionic acid, are particularly suitable for the process according to the invention. Propionic acid, and thus perpropionic acid, is very particularly suitable.

Suitable solvents for the solution of the percarboxylic acids, used for introducing further hydroxyl groups into the aromatic nucleus of phenols, are all the organic solvents which are inert towards the percarboxylic acid. Examples which prove suitable are aromatic (particularly carbocyclic aromatic) hydrocarbons which contain six to ten carbon atoms, aliphatic or cycloaliphatic (particularly saturated aliphatic or cycloaliphatic) hydrocarbons, in each case containing up to twelve carbon atoms, chlorinated hydrocarbons (such as chlorinated alkanes) which contain one to ten carbon atoms and one to four chlorine atoms, and esters of carboxylic acids (particularly alkyl esters of alkane carboxylic acids), containing one to five C atoms, with straight-chain or branched alcohols in which one to eight C atoms are present in the molecule, as well as ethers which contain up to 10 C atoms. Examples of suitable solvents which may be mentioned are benzene, toluene, n-pentane, isooctane, cyclohexane, methylene chloride, chloroform, 1,2-dichloroethane, 1,2-dichloropropane, methyl ethyl acetate, n-propyl acetate, isopropyl acetate, n-butyl acetate, isoamyl acetate, methylpropionate, ethylpropionate, propylpropionate and butylpropionate, as well as chlorobenzene and ether. However, it is also possible to mixtures of the solvents mentioned, as solvents for the percarboxylic acid, the components of the mixture then being advantageously chosen so that they have a similar boiling point. Chlorinated hydrocarbons, such as methylene chloride, dichloroethane or dichloropropane, or aromatic hydrocarbons, such as benzene or toluene, or mixtures of these solvents are preferably used. Benzene is very particularly preferably used as the solvent for the process according to the invention.

Choosing the type of percarboxylic acid and choosing the type of solvent for the percarboxylic acid depends on the phenolic compounds into which the additional hydroxyl groups are to be introduced, and above all on the boiling point thereof. In general, a percarboxylic acid, the corresponding carboxylic acid of which has a lower boiling point than the substituted phenol, and a solvent which has a boiling point which is either lower than the boiling point of the carboxylic acid corresponding to the percarboxylic acid or which is between the boiling point of the phenolic compound and that of the carboxylic acid are used for the process according to the invention. However, it is also possible to choose the solvent and carboxylic acid so that both the solvent and the carboxylic acid have a higher boiling point than the phenolic compound. However, it is advantageous, in particular when the phenolic compound is employed in excess in the reaction with the organic solution of the percarboxylic acid, to choose the carboxylic acid and solvent so that they both have lower boiling points than the polyhydric phenols formed during the reaction. A percarboxylic acid, the corresponding carboxylic acid of which has a boiling point, under normal pressure, which is at least 10° C., particularly preferably at least 30° C., below the boiling point of the phenolic compound being used in the reaction is preferably used in the process according to the invention. Amongst the compounds already listed, a solvent which has a boiling point, under normal pressure, at least 10° above or at least 10° below, particularly preferably at least 20° below, the boiling point of the carboxylic acid corresponding to the percarboxylic acid is preferably chosen as the inert solvent for the percarboxylic acid.

In addition, the percarboxylic acid, or the carboxylic acid corresponding to this, and the solvent for the process according to the invention are advantageously chosen so that no pronounced azeotropes of a binary or ternary nature occur within the combination carboxylic acid/solvent, phenol to be reacted.

The solution of the percarboxylic acid in the inert organic solvent can be prepared in a known manner. Thus, a solution of this type can be obtained by oxidising an aldehyde to the corresponding percarboxylic acid, using oxygen or oxygen-containing gases. However, it is also possible to subject an ester of a carboxylic acid with an alcohol which has a lower boiling point than the inert organic solvent to a perhydrolysis with hydrogen peroxide and thereafter to distill off the alcohol formed and the water. The organic solution of the percarboxylic acid is obtained in a manner which is advantageous industrially, for example according to the process of German Patent specification No. 2,262,970, by extracting a reaction mixture, containing by reaction of hydrogen peroxide, water, an acid catalyst and a carboxylic acid, with the inert organic solvent and, if appropriate, subsequently drying the extract, which essentially contains the percarboxylic acid.

Phenols which can be employed in accordance with the process according to the invention should have a water content which is as low as possible. In general, it is sufficient if the content of water is less than 2% by weight. Phenolic compounds which contain less than 1% by weight of water are preferably used.

The phenolic compound from which a polyhydric phenol is to be prepared can be reacted with the organic solution of the percarboxylic acid in the form of a solution. However, it is also possible to react the pure phenol with the percarboxylic acid solution. If the phenolic compound is employed in solution, the solvent in which the percarboxylic acid is dissolved is preferably chosen. The phenolic compound being reacted is itself particularly preferably used as the solvent.

The ratio of the percarboxylic acid to the phenolic compound being reacted can vary within wide limits. In general, it is advantageous to choose the molar ratio so that the amount of phenol is in excess of that needed to provide the hydroxyl group to be additionally introduced. For example, the molar ratio is about 1 to 50 mols preferably about 10 to 30 mols of phenolic compound per mol of percarboxylic acid. In the process according to the invention, during the reaction of some phenols, still containing a free hydrogen atom in the para-position to the hydroxyl group which is already present in the aromatic nucleus and which gives rise to the phenolic character, after the introduction of a further hydroxyl group (see equation 1) into this position, small amounts of the corresponding quinone are sometimes formed from the now dihydric phenolic compound by reaction with the percarboxylic acid (see equation 2), which, however, is not troublesome since this quinone-like compound can be reconverted into the dihydric phenol in a simple manner (see equation 3). This course of the reaction can be illustrated with the aid of the following equations for the use of 2-methoxyphenol

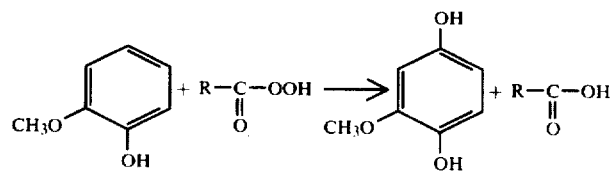

(Equation 1)

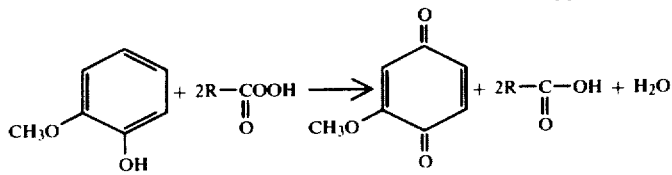

(Equation 2)

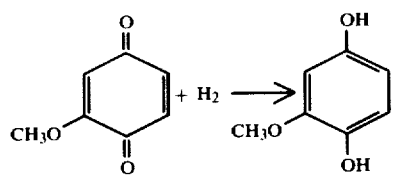

(Equation 3)

As a rule, two or more isomeric dihydric phenols are formed from the phenols by the process according to the invention. However, the number of isomers depends decisively on the nature and the number of the substituents which replace one or more hydrogen atoms in the aromatic nucleus of the phenols. In the case of mononuclear or polynuclear phenols, the o-position and p-position of which relative to the hydroxyl group present are not occupied by substituents, virtually exclusively o-hydroxylated and p-hydroxylated products are formed when, for example, the ratio of percarboxylic acid to phenolic compound is chosen so that only one further hydroxyl group is introduced.

The temperatures at which the reaction of the phenolic compound with the organic solutions of the percarboxylic acid is carried out are about −20° C. to about 120° C., preferably about 0° C. to 100° C., particularly preferably between 20° C. and 80° C. and very particularly preferably about 30° C. to 50° C.

The pressure is not decisive for the reaction. In principle, the reaction can be carried out under elevated pressure or under normal pressure or under reduced pressure. All or some of the reactants can be present in the gaseous form. In order to remove the heat of reaction, the mixture can be cooled with a suitable medium. In order to set the desired reaction temperature exactly, the pressure in the reaction vessel is chosen, for example, so that the reaction mixture just boils. Devices which are customary for conversions of this type can be used for carrying out the reaction, such as stirred kettles, tube reactors or loop reactions. In general, when the reaction is carried out continuously, a device which behaves as a cascade of at least two ideally mixed kettles is used. It is particularly advantageous to use a reaction system which behaves as a cascade of 4 to 50, preferably 10 to 30, ideally mixed kettles. However, it is also possible to carry out the reaction discontinuously. Suitable materials from which the devices for carrying out the reaction can be manufactured are glass, enamel or alloyed stainless steels.

The reaction time depends on the phenolic compound into which the additional hydroxyl group is to be introduced, but also on the temperature and the concentration in the percarboxylic acid and of the phenol, as well as of the solvent in which the percarboxylic acid is being employed. As a rule, the reaction conditions, such as temperature, pressure and concentrations, are chosen so that the percarboxylic acid is converted to the extent of over 98% after 0.25 to 3 hours, preferably from 0.5 to 2 hours.

The reaction mixture is worked up by customary methods by fractional distillation, preferably in vacuo, the solvent for the percarboxylic acid being initially recovered in a first stage, and thereafter the carboxylic acid corresponding to the percarboxylic acid being recovered in a second distillation unit. Thereafter, if the phenolic compound has been employed in excess in the reaction, this phenol is first recovered and then the polyhydric phenols are isolated. However, it is also possible first to separate off the solvent and the carboxylic acid by distillation and thereafter to obtain the polyhydric phenols by fractional crystallisation. The reaction mixture can also be worked up by extraction or by a combination of the extraction process and the distillation process.

The carboxylic acid recovered and the organic solvent recovered during the working up of the reaction mixture are advantageously re-used for the preparation of the organic solution of the percarboxylic acid. The phenolic compound which may be recovered during the working up is preferable recycled to the reaction with the percarboxylic acid, if appropriate after intermediate purification, but can also be employed in another application.

In a particular embodiment of the process according to the invention, a solution, which is non-aqueous and essentially free from hydrogen peroxide and which contains 10 to 35% by weight of perpropionic acid and 5 to 25% by weight of propionic acid, of perpropionic acid in benzene or dichloropropane is added to a solution, which is stirred and warmed to 20° C. to 100° C., of a 4-alkyl-1-hydroxy-benzene in benzene or in dichloropropane, or to the melt of this phenol, in such a way that the temperature can be kept within the range indicated. The perpropionic acid solution being reacted with the phenol contains less than 1% by weight of water and not more than 1% by weight of the hydrogen peroxide. The molar ratio of 4-alkyl-1-hydroxybenzene to perpropionic acid is 5 to 25:1.

The time required for the addition of the solution of the perpropionic acid is 3 to 30 minutes. After 10 minutes to 2 hours, calculated from the end of the addition of the solution, the perpropionic acid is converted to the extent of more than 98%. After cooling, it can be determined in the reaction mixture, by analysis by gas chromatography, that the 4-alkyl-1,2-dihydroxybenzene has been formed with a selectivity of 85 to 95%, relative to the percarboxylic acid employed in the reaction.

After distilling off the solvent and the propionic acid under 500 to 100 mm Hg, the excess monohydric phenol is recovered by a further rectification step, also carried out under reduced pressure, after which the 4-alkyl-1,2-dihydroxybenzene is obtained as an already very pure product of 95 to 99% purity, and, if the particular intended use demands, can be further purified by distillation or recrystallisation.

EXAMPLE 1

25.2 g of a 10.5% strength by weight solution of perpropionic acid in benzene, which also contains 6.2% by weight of propionic acid, 0.12% by weight of hydrogen peroxide and less than 0.1% by weight of water in addition to the perpropionic acid, are added dropwise to 123.7 g of a 52% strength by weight solution, warmed to 80° C., of 2-chlorophenol in 1,2-dichloropropane in the course of 8 minutes, whilst stirring. After the dropwise addition of the perpropionic acid solution has ended, the mixture is kept at this temperature for a further 1.5 hours, and the conversion of perpropionic acid is then determined and at this time is already 90.6%. The mixture is therefore stirred for a further 33 minutes at 80° C. After this time, the perpropionic acid is completely converted. After cooling the reaction mixture, the amounts of diphenols obtained are determined by means of analysis by gas chromatography. It is found that 2 g (=13.78 mmols) of 1-chloro-2,5-dihydroxybenzene and 1.7 g (=11.7 mmols) of 1-chloro-2,3-dihydroxybenzene are contained in the mixture, which corresponds to a total selectivity for diphenols of 86.7%, relative to the perpropionic acid employed in the reaction.

EXAMPLE 2

15 g of an 18.6% strength by weight solution of perisobutyric acid in 1,2-dichloropropane are added to a melt, stirred and warmed to 40° C., of 48.9 g (=0.4 mol) of 1,3,4-xylenol. In addition to perisobutyric acid, the solution contains 11.9% by weight of isobutyric acid, 0.1% by weight of hydrogen peroxide and 0.18% by weight of water. After the perisobutyric acid solution has been added, a temperature increase to 56° C. is detected in the course of 7 minutes. After the evolution of heat has subsided, the reaction is brought to completion at 45° C., which requires 35 minutes at this temperature. After this time, a complete perisobutyric acid conversion is achieved. 3.42 g (=24.7 mmols) of 1,2-dihydroxy-3,5-dimethyl-benzene are detected in the reaction mixture, which corresponds to a yield of this product of 92.4%, relative to the perisobutyric acid employed.

EXAMPLE 3

50 g (=0.0294 mol) of 4-hydroxybiphenyl are dissolved in 200 ml of ethyl acetate, and after the solution has first been warmed to 60° C., whilst stirring, 15.7 g of a 9.5% strength by weight solution of peracetic acid in ethyl acetate, which also contains small amounts of acetic acid and 0.15% by weight each of water and hydrogen peroxide in addition to the peracetic acid, are added in a manner such that the temperature of the mixture does not rise above 62° C. After the addition of the peracetic acid solution has ended, the mixture is then stirred for a further 2 hours at 62° C. After this time, the conversion of peracetic acid is determined as 98.7%. It is established, by analysis by gas chromatography, that at this point in time 3.31 g (=17.8 mmols) of 1,2-dihydroxy-4-phenylbenzene are present in the reaction mixture. The yield of this product is thus 90.7%, relative to the peracetic acid employed.

EXAMPLE 4

200 g of 3-methyl-4-tert.-butyl-1-naphthol are dissolved in 500 ml benzene. After this solution has been warmed to 40° C., whilst stirring, 60 g of a 17.6% strength by weight solution of perpropionic acid in benzene are added. The perpropionic acid solution also contains 0.2% by weight of water and 11.2% by weight of free propionic acid, in addition to 0.35% by weight of hydrogen peroxide. In order to achieve complete conversion of the perpropionic acid, a reaction time of 2.5 hours is required at a temperature of 55° C. After this time, the mixture is cooled and analysed. It is found that 23.86 g (=0.1 mol) of 1,2-dihydroxy-3-methyl-4-tert.-butyl-naphthalene have been formed, which corresponds to a yield of 88.4%, relative to the perpropionic acid employed.

EXAMPLE 5

150 g (1 mol) of p-tert.-butylphenol in 500 ml of benzene are initially introduced into a 1 l round-bottomed flask, thermostatically controlled at 45° C., and 31.5 g of a 20.4% strength by weight solution of perpropionic acid in benzene, which has a water content of less than 0.01% by weight, are added dropwise under a slight excess pressure of nitrogen, whilst stirring. The rate of the dropwise addition is adjusted so that the temperature in the flask does not rise above 50° C. After stirring for two hours at 45° C., perpropionic acid can no longer be detected in the reaction mixture; the content of p-tert.-butylpyrocatechol in the mixture, determined by gas chromatography, is 11 g, corresponding to a yield of 93%, relative to the perpropionic acid employed.

EXAMPLE 6

149 g of a 16% strength by weight solution of perpropionic acid in 1,2-dichloropropane are added, at room temperature, to 325 g of m-cresol (3 mols); the peracid solution contains 0.35% by weight of water and 0.15% by weight of hydrogen peroxide, as well as 9.8% by weight of propionic acid. The reaction mixture is stirred at 70° C. for 30 minutes under an inert gas; after this time, an analysis to determine active oxygen shows complete conversion of the perpropionic acid.

The yield is 27.5 g of dihydroxymethylbenzenes; these consist of 3,4-dihydroxytoluene, 2,5-dihydroxytoluene and 2,3-dihydroxytoluene, which are present in the ratio 5:3:0.8. This total yield of dihydroxymethylbenzenes corresponds to 89%, relative to the perpropionic acid employed.

EXAMPLE 7

Per hour, 500 g of a 30% strength by weight benzene solution, warmed to 50° C., of thymol (=1 mol per hour) and 21 g of a 25% strength by weight solution of perisobutyric acid in benzene are fed into a two-stage kettle cascade with a reaction volume of 1 l per kettle. The water content of the perisobutyric acid solution is between 0.15 and 0.3% by weight. The reaction mixture was blanketed with argon and the temperature in the first kettle is 60° C. and in the second kettle is 70° C.

Perisobutyric acid can no longer be detected in the solution leaving the cascade. 4 g of 1,2-dihydroxy-3-isopropyl-6-methylbenzene and 3.5 g of 1,4-dihydroxy-2-isopropyl-5-methylbenzene per hour are obtained in this solution.

This corresponds to a yield of the dihydroxybenzenes of 89%, relative to the perisobutyric acid.

EXAMPLE 8

950 g (6 mols) of 4-methylnaphthol (-2) are dissolved in 5 l of n-butyl acetate. This solution is warmed to 55° C. in an enamelled 10 l reaction vessel, which is provided with a stirring device, under nitrogen and thereafter 130 g of a 19% strength by weight solution of peracetic acid in n-butyl acetate, in which water and hydrogen peroxide are present in a proportion of 0.2% by weight each, are added dropwise in the course of 30 minutes. After stirring for a further 60 minutes under nitrogen at 55° C., the conversion of the peracetic acid is complete. After cooling, 53 g of 1,2-dihydroxy-4-methylnaphthalene are found in the reaction mixture, which corresponds to a yield of 93.9%, relative to the peracetic acid employed.

What is claimed is:

1. Process for the preparation of a dihydric substituted phenol which essentially comprises reacting, a solution, which contains less than 5% by weight of water less than 2% by weight of hydrogen peroxide, and less than 1% by weight of a free strong acid or of a salt of such acid, of a percarboxylic acid having 1 to 18 carbon atoms in an inert organic solvent with a monohydric substituted phenol of the formula

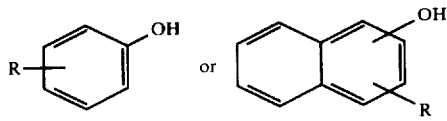

wherein
R represents $C_1$-$C_{10}$-alkyl, $C_3$-$C_{12}$-cycloalkyl, phenyl, naphthyl, fluorine, chlorine or bromine, or a nitro, cyano, sulphonic acid, carbohydroxyl, carbo-$C_1$-$C_{10}$-alkoxy, $C_1$-$C_3$-alkoxy or $C_1$-$C_4$-dialkylamino group, said alkyl and cycloalkyl radicals defining R being unsubstituted or substituted by fluorine, chlorine or bromine atoms or $C_1$-$C_5$-alkoxy, $C_1$ to $C_4$-dialkylamino, carboxyl, nitro, cyano, sulphonic acid or $C_1$ to $C_{10}$-carbalkoxy groups, and said phenyl and naphthyl radicals defining R being unsubstituted or substituted by fluorine, chlorine, bromine, $C_1$-$C_{10}$-alkyl or $C_3$-$C_{12}$-cycloalkyl, as well as nitro, carbohydroxyl, carbo-$C_1$-$C_{10}$-alkoxy, $C_1$-$C_5$-alkoxy, cyano, sulphonic acid or $C_1$-$C_4$-dialkylamino groups at a temperature from about −20° C. to about 120° C.

2. Process according to claim 1, characterized in that a compound of the formula

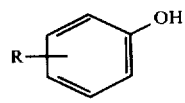

wherein
R represents $C_1$-$C_{10}$-alkyl, $C_3$-$C_{12}$-cycloalkyl, phenyl, naphthyl, fluorine, chlorine or bromine, or a nitro, cyano, sulphonic acid, carbohydroxyl, carbo-$C_1$-$C_{10}$-alkoxy, $C_1$-$C_3$-alkoxy or $C_1$-$C_4$-dialkylamino group, said alkyl and cycloalkyl radicals R being unsubstituted or substituted by fluorine, chlorine or bromine atoms or $C_1$-$C_5$-alkoxy, $C_1$ to $C_4$-dialkylamino, carboxyl, nitro, cyano, sulphonic acid or $C_1$ to $C_{10}$-carbalkoxy groups, and said phenyl and naphthyl radicals R being unsubstituted or substituted by fluorine, chlorine, bromine, $C_1$-$C_{10}$-alkyl or $C_3$-$C_{12}$-cycloalkyl, as well as nitro, carbohydroxyl, carbo-$C_1$-$C_{10}$-alkoxy, $C_1$-$C_5$-alkoxy, cyano, sulphonic acid or $C_1$-$C_4$-dialkylamino groups is used as the monohydric substituted phenol.

3. Process according to claim 2, characterized in that

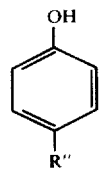

wherein
R″ denotes $C_1$-$C_5$-alkyl, $C_5$-$C_7$-cycloalkyl, phenyl, fluorine or chlorine, or a nitro, sulphonic acid, carbohydroxyl, carbo-$C_1$-$C_3$-alkoxy, $C_1$-$C_3$-alkoxy or $C_1$-$C_2$-dialkylamino group, is employed as the monohydric substituted phenol.

4. Process according to claim 1, characterized in that an organic solution of the percarboxylic acid with a content of less than 1% by weight of water and less than 1% by weight of hydrogen peroxide is employed.

5. Process according to claim 1, characterized in that an organic solution of the percarboxylic acid with a content of less than 0.5% by weight of water and less than 0.5% by weight of hydrogen peroxide is employed.

6. Process according to claim 1, characterized in that an organic solution of the percarboxylic acid with a content of less than 0.5% by weight of a strong acid is used.

7. Process according to claim 1, characterized in that an organic solution of the percarboxylic acid with a content of less than 0.1% by weight of a strong acid is used.

8. Process according to claim 1, characterized in that the concentration of percarboxylic acid in the organic solution is 5–50% by weight.

9. Process according to claim 1, characterized in that the concentration of percarboxylic acid in the organic compound is about 10 to 30% by weight.

10. Process according to claim 1, characterized in that the percarboxylic acid contains two to five carbon atoms.

11. Process according to claim 1, characterized in that the solution of percarboxylic acid is a solution of perpropionic acid.

12. Process according to claim 1, characterized in that benzene, toluene or dichloropropane is used as the inert organic solvent for the percarboxylic acid.

13. Process according to claim 12, characterized in that benzene is used as the inert organic solvent.

14. Process according to claim 1, characterized in that a percarboxylic acid is employed, the corresponding carboxylic acid of which has a boiling point, under normal pressure, which is at least 30° C. below the boiling point of the phenol.

15. Process according to claim 1, characterized in that a solvent which has a boiling point, under normal pressure, at least 20° C. below that of the carboxylic acid corresponding to the percarboxylic acid is used as the inert, organic solvent for the percarboxylic acid.

16. Process according to claim 1, characterized in that a solution, which has been obtained by extracting a mixture containing hydrogen peroxide, water, a free strong acid or a salt of such acid as an acid catalyst and the percarboxylic acid with the inert organic solvent, is used as the solution of the percarboxylic acid in an inert organic solvent.

17. Process according to claim 1, characterized in that the reaction between the organic solution of the percarboxylic acid and the substituted phenol is carried out at temperatures from about −20° to 120° C.

18. Process according to claim 1, characterized in that the phenol being reacted with the organic solution of the percarboxylic acid contains less than 1% by weight of water.

19. Process according to claim 1, characterized in that the carboxylic acid, recovered during the working up of the reaction mixture and the solvent recovered during the working up, are fed to the preparation of the organic solution of the percarboxylic acid.

* * * * *